United States Patent [19]

Eden et al.

[11] Patent Number: 5,672,484
[45] Date of Patent: Sep. 30, 1997

[54] MICROBIOLOGICAL CULTURE BOTTLE, AND METHOD OF MAKING AND USING SAME

[75] Inventors: Ruth Eden; Gideon Eden; Ray McMillian, all of Ann Arbor, Mich.

[73] Assignee: Difco Laboratories, Ann Arbor, Mich.

[21] Appl. No.: 576,050

[22] Filed: Dec. 21, 1995

Related U.S. Application Data

[63] Continuation of Ser. No. 191,982, Feb. 4, 1994, abandoned.

[51] Int. Cl.$^6$ ............................................. C12Q 1/04
[52] U.S. Cl. .................. 435/29; 435/34; 435/287.7; 435/288.1; 435/299.1; 435/299.2; 435/39
[58] Field of Search ............................. 435/34, 287.7, 435/288.1, 288.2, 299.1, 299.2, 29, 39

[56] References Cited

U.S. PATENT DOCUMENTS

| | | | |
|---|---|---|---|
| 2,904,474 | 9/1959 | Forg | 435/287.7 |
| 3,107,204 | 10/1963 | Brown et al. | 435/287.7 X |
| 4,152,213 | 5/1979 | Ahnell | 435/34 |
| 4,812,656 | 3/1989 | Yamakawa et al. | 250/363.01 |
| 5,047,331 | 9/1991 | Swaine et al. | 435/29 |
| 5,100,783 | 3/1992 | Dean et al. | 435/240.23 |
| 5,217,876 | 6/1993 | Turner et al. | 435/69.1 |
| 5,232,839 | 8/1993 | Eden et al. | 435/39 |

*Primary Examiner*—Milton Cano
*Attorney, Agent, or Firm*—Kohn & Associates

[57] ABSTRACT

A container (10) adapted for use in the detection of aerobic microorganisms in a sample includes a non-toxic insert (22) disposed within the container (10) for supporting microorganisms adhered thereto and for increasing microbial exposure to oxygenated growth media to enhance microbial metabolism. A method for making the container (10) includes the steps of inserting a non-toxic insert (22) into the container (10) and adding growth media (14). Also, a method of detecting aerobic microbiological growth in a sealed sample container (10) having a headspace (16) and which contains a sample which may contain an unknown microorganism includes the steps of providing a sealed sample container (10) having a headspace (16) and non-toxic insert (22) saturated with microbiological growth media (24), inoculating the insert (22) within the sealed sample container (10), and monitoring metabolism in the container (10) as an indicator of the presence of microorganisms to detect microorganisms in the sample.

8 Claims, 5 Drawing Sheets

MICROBIOLOGICAL CULTURE BOTTLE, AND METHOD OF MAKING AND USING SAME

This is a continuation of application Ser. No. 08/191,982 filed on Feb. 4, 1994, now abandoned.

BACKGROUND OF THE INVENTION

1. Technical Field

The present invention generally relates to the detection of aerobic microorganisms. More particularly, the present invention relates to a culture bottle for use in systems for detecting aerobic microorganisms

2. Background Art

Culturing bodily fluids such as blood, sputum, and urine is commonly employed in the medical field in order to ascertain the presence or absence of microorganisms.

Typically, a sample of bodily fluid to be tested is obtained from a patient. The sample is then analyzed in order to determine the presence or absence of microorganisms. Several methods of determining the presence or absence of microorganisms are commonly employed. The most common technique employed involves preparing a culture by inoculating a growth medium with a sample of the bodily fluid and incubating the culture. After sufficient incubation, a visual inspection by a technician is performed in order to observe and assess for the presence or absence of bacterial growth.

It is the standard practice in microbiology to detect the presence and assess numbers of microorganisms in samples. Medical test samples include body fluids such as blood, spinal fluid and urine. Industrial samples include pharmaceuticals, foods and any other sample that must be tested for presence or levels of organisms. All such samples are cultured by inserting them into a vessel containing sterile growth medium. The growth medium contains the appropriate nutrient to support the growth of the target organisms.

Microbial presence is detected through changes in the liquid medium or in the atmosphere over the specimen after a period of time. For example, U.S. Pat. No. 4,812,656 to Ahnell et al. uses media with carbon 13 labelled substrates. After subjecting the sample to conditions conducive to microbial growth, the ratio of carbon 13 to carbon 12 in the gaseous atmosphere is determined. U.S. Pat. No. 5,232,839 to Eden et al., assigned to the assignee of the present invention and herein incorporated by reference, discloses a method for timely detecting microbiological growth in a sealed container by monitoring consumption of the oxygen in the headspace or production of $CO_2$ or any other gas as an indication of microbial metabolism. U.S. Pat. No. 5,217,876 describes a $CO_2$ sensor present at the bottom of a vial, which detects presence of microorganisms by detecting changes in the pH of the specimen or the production of $CO_2$. U.S. Pat. No. 5,047,331 to Swaine et al. discloses a blood culturing bottle including a sterile container and nutrient growth media, whereby increase in pressure in the head space is monitored.

Other known methods for measuring microbial contamination in samples include measuring minute changes in temperature, pH, turbidity, color, bioluminescence and impedance. All these methods determine microbial contamination by determining microbial end products or metabolites.

For diagnostic purposes it is advantageous to determine as quickly as possible whether or not any microorganisms are present in a clinical sample. Diagnosis and the commencement of efficacious drug therapy are greatly enhanced by prompt evaluation of a clinical sample for the presence or absence of microorganisms. Therefore, optimizing a microorganism's growth speeds up the diagnostic process. In order to achieve optimal growth rates of aerobic microorganisms, the concentration of dissolved oxygen in the culture can be increased. In other words, preventing the culture medium from becoming anaerobic enhances aerobic microbial growth.

Oxygen has a low solubility in water and poor diffusion across the air-water interface limits attainable oxygen concentration in the culture medium. Shaking, agitating, or bubbling air through a porous sparger may be used to increase the dissolved oxygen content in the culture. Shaking, agitating, or bubbling air through the culture increases the amount of oxygen in the growth medium and, thereby, increases oxygenation of the aerobic bacteria enhancing their metabolism and growth while preventing the culture medium from becoming anaerobic. In order to achieve better oxygen concentrations in the growth media-agitation of the bottles during growth is taught. (U.S. Pat. No. 5,047,331 and U.S. Pat. No. 5,217,876). However, shaking or agitating a culture requires more complex and expensive apparatuses, adds a potential for culture bottle or tube breakage or contamination, and can cause splashing of the culture. Additionally, the shaking apparatus is typically expensive and is prone to mechanical difficulty or failure.

It would, therefore, be advantageous to provide means for increasing oxygenation of the bacteria by increasing the amount of oxygen available to the organism in the medium thereby, increasing the oxygenation of the aerobic bacteria and enhancing their metabolism and growth rate without the need for shaking, agitating, or bubbling air through the media.

The present invention provides a container adapted for use in the detection of aerobic microorganisms, including a non-toxic insert which can hold microorganisms in suspension and increase microbial exposure to oxygenated media and enhance microbial metabolism. A method for making the container is further provided. Finally, the present invention provides a process for detecting aerobic microbiological growth utilizing the novel container of the present invention.

SUMMARY OF THE INVENTION

In accordance with the present invention, there is provided a container for use in the detection of aerobic microorganisms in a sample, the container including an inner chamber and a non-toxic insert, which increases surface area, the insert disposed within the inner chamber for supporting microorganisms suspended within or on the insert thereof to increase microbial exposure to oxygenated media and enhance microbial metabolism.

The present invention further provides a method of making the container by the steps of inserting an non-toxic insert into a container adding microbial growth media and sterilizing the bottle container.

Additionally, the present invention provides a process of detecting aerobic microbiological growth in a sealed sample container having a headspace and which contains a sample which may contain an unknown microorganism, including the steps of providing a sealed sample container having a headspace and non-toxic insert saturated with microbiological growth media, inoculating the insert within the sealed sample container, and monitoring metabolism within the container as an indicator of the presence of microorganisms to detect microorganisms in the sample.

FIGURES IN THE DRAWINGS

Other advantages of the present invention will be readily appreciated as the same becomes better understood by reference to the following detailed description when considered in connection with the accompanying drawings wherein.

Figure 3A:
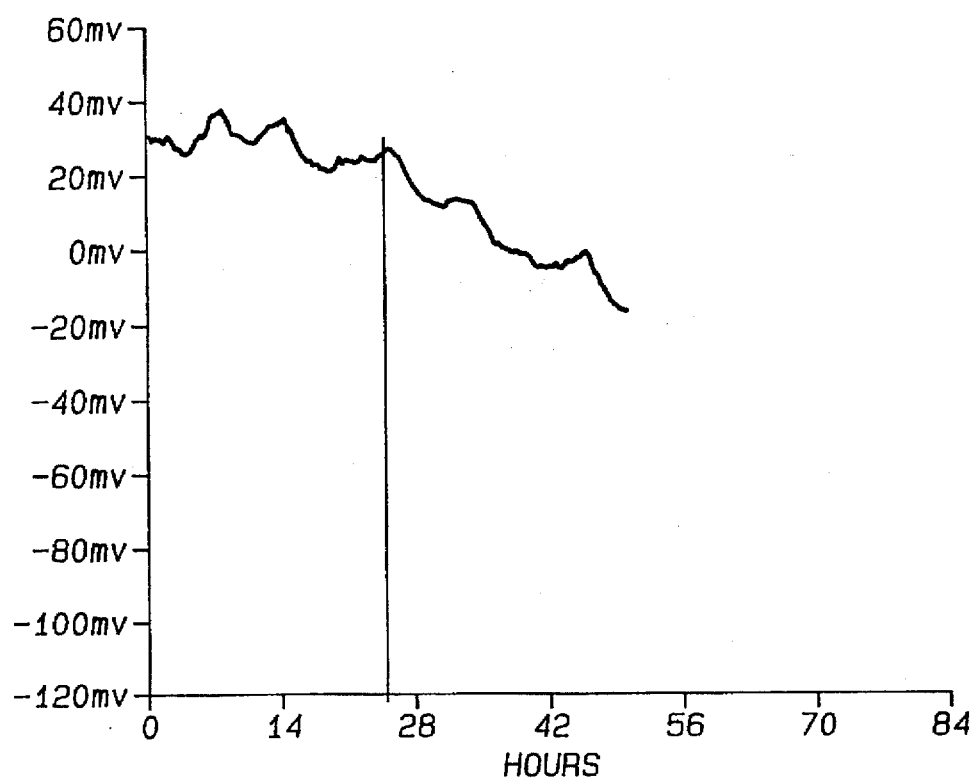
Figure 3B:
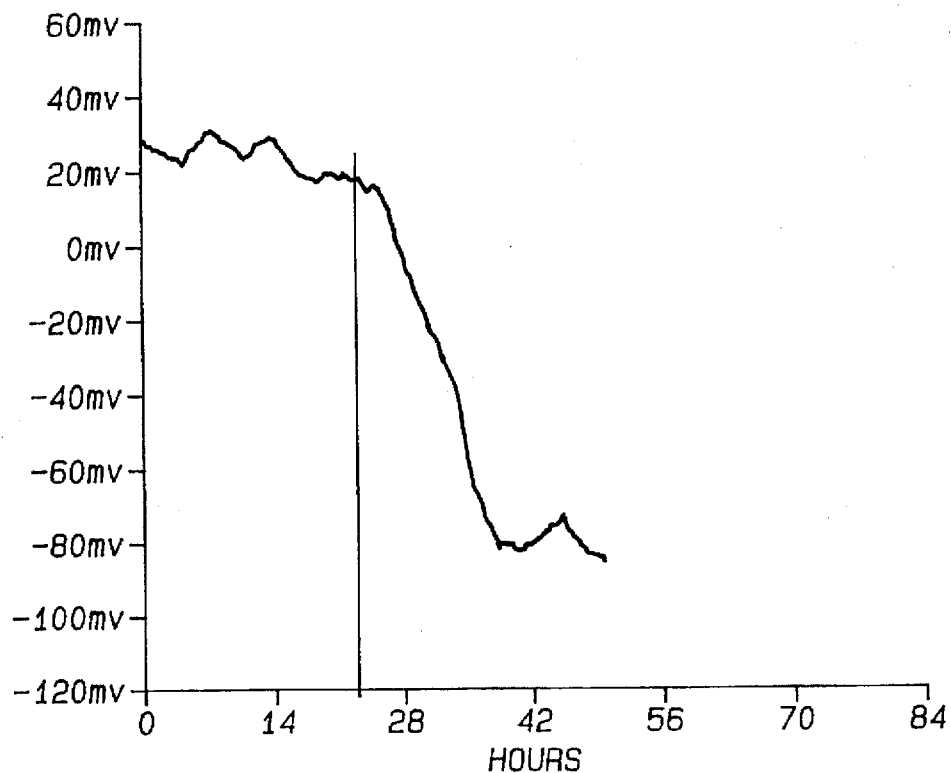

FIG. 3a as a graphic illustration of pressure change an a sample containing M. tuberculosis in a 40% oxygen environment without the sponge insert; and FIG. 3b is a graphic illustration of pressure change an a sample containing M. tuberculosis in a 40% oxygen environment with the sponge insert.

Figure 4A:
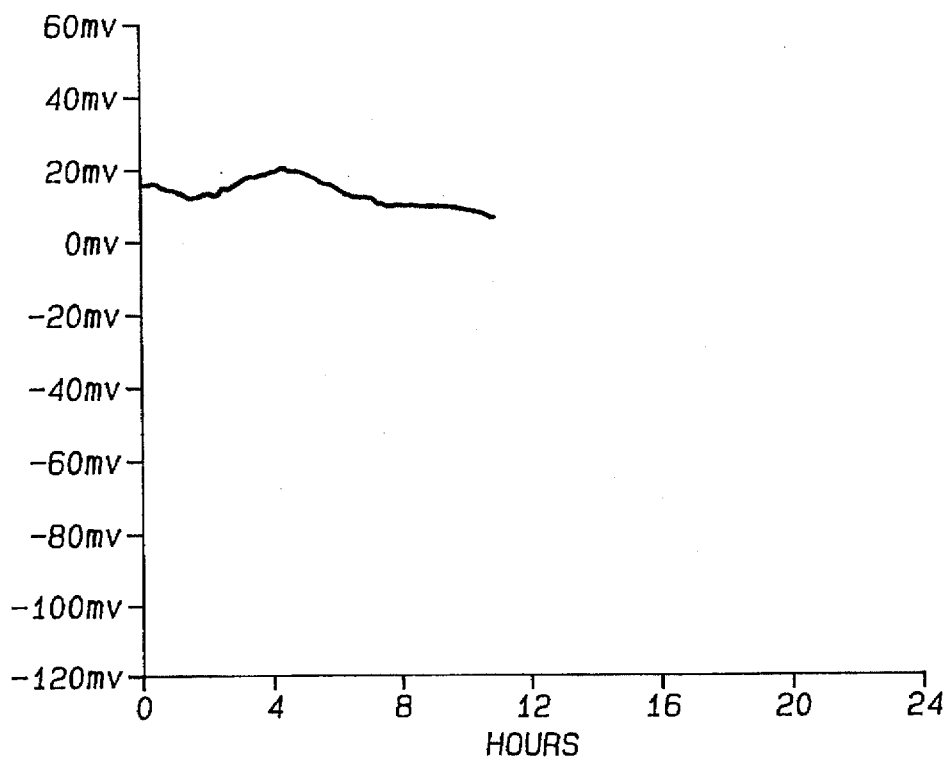

FIG. 4a is a graphic illustration of pressure change an a sample containing C. neoformans in a 20% oxygen environment without the sponge insert.

Figure 4B:
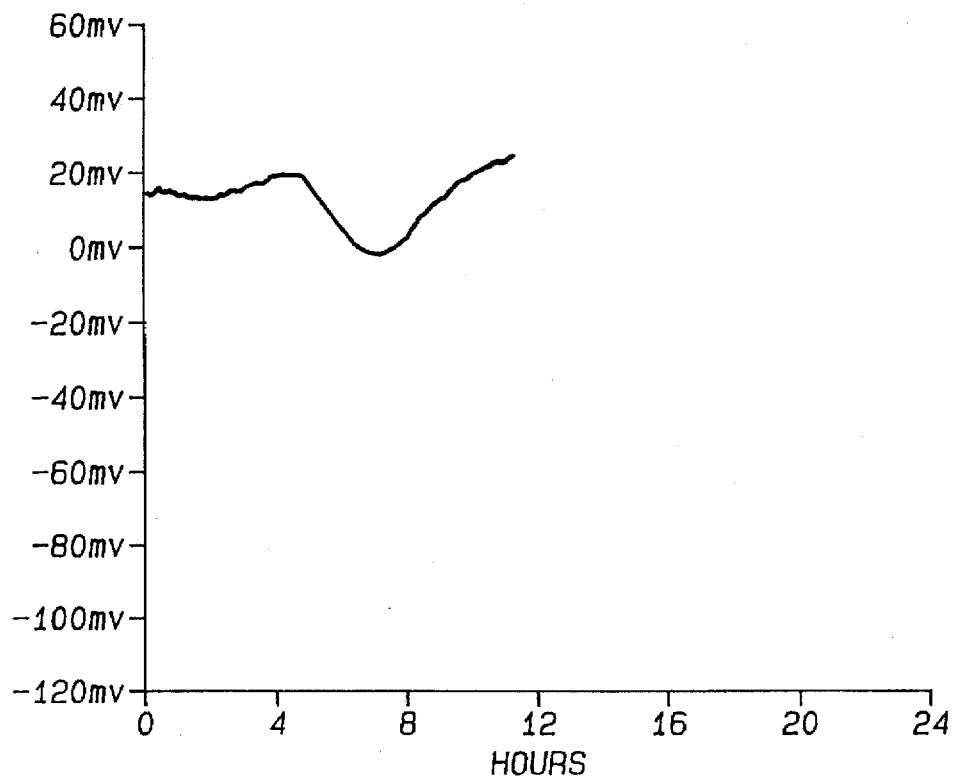

FIG. 4b is a graphic illustration of pressure change an a sample containing C. neoformans in a 20% oxygen environment with the sponge insert.

Figure 5A:
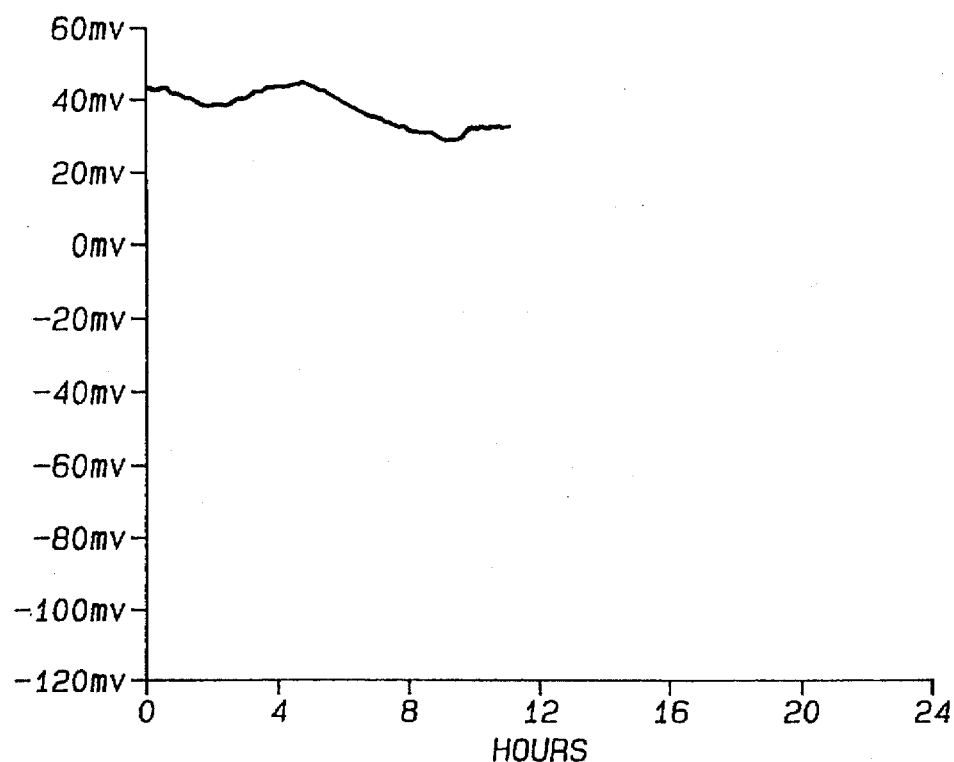
Figure 5B:
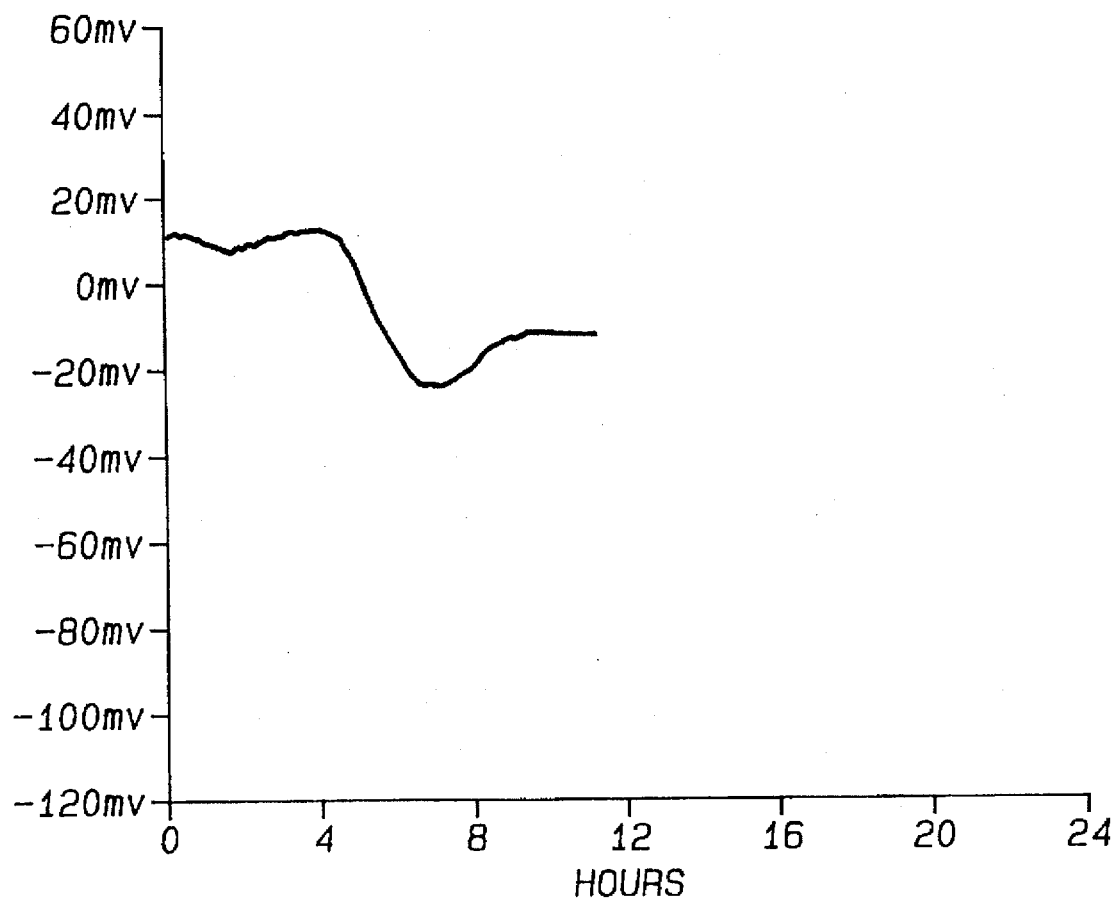

FIG. 5a as a graphic illustration of pressure change an a sample containing C. neoformans in a 40% oxygen environment without the sponge insert; and FIG. 5b is a graphic illustration of pressure change in a sample containing C. neoformans in a 40% oxygen environment with the sponge insert.

DETAILED DESCRIPTION OF THE INVENTION

Figure 1:
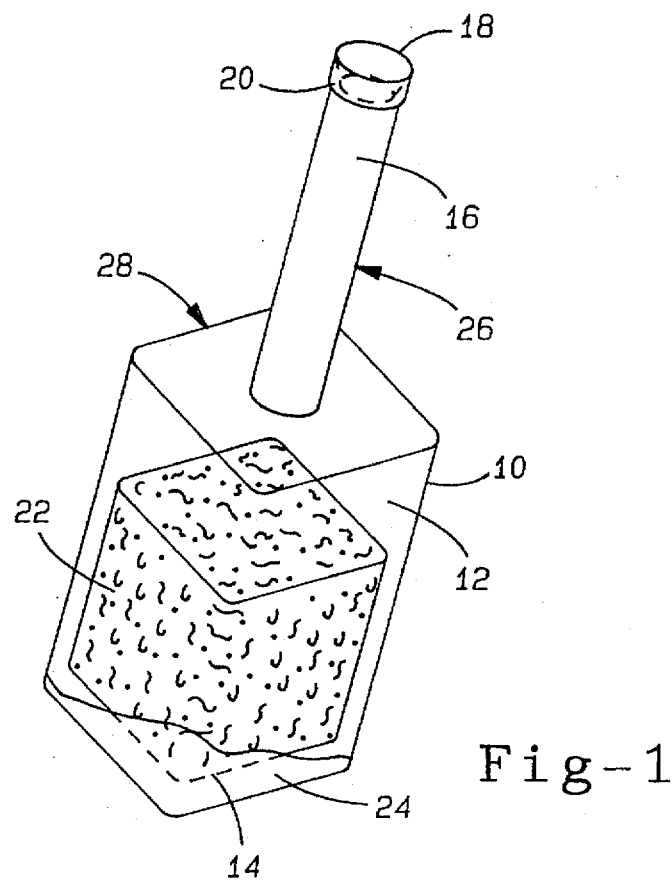
FIG. 1 is a perspective view of the microbiological culture bottle of the present invention.
Figure 2A:
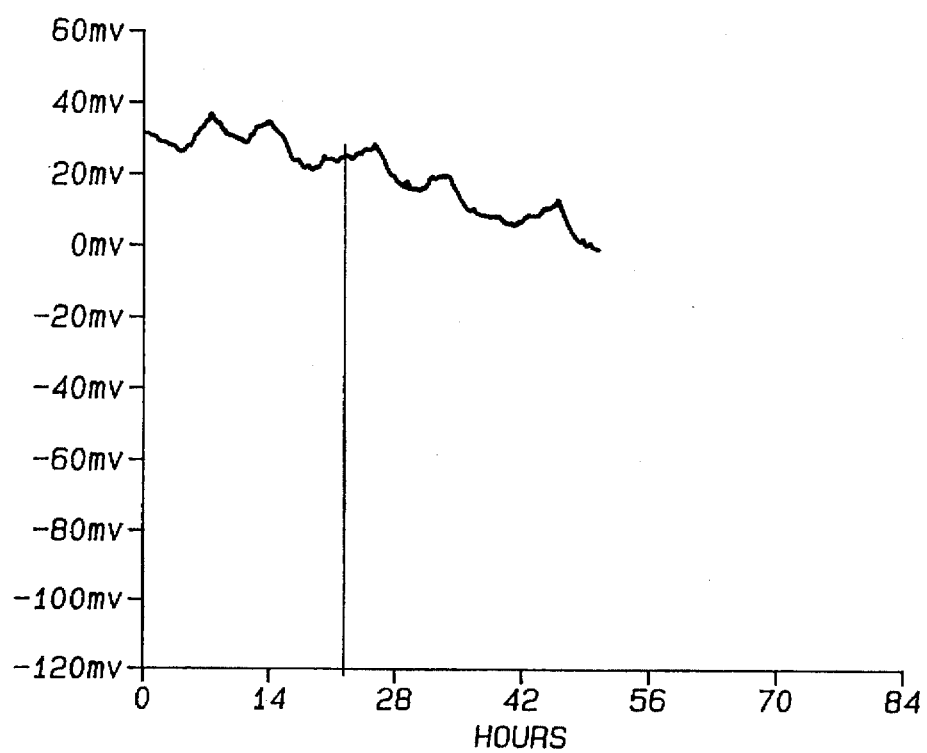
FIG. 2a is a graphic illustration of pressure change in a sample for containing M. tuberculosis in a 20% oxygen environment without the sponge insert.
Figure 2B:
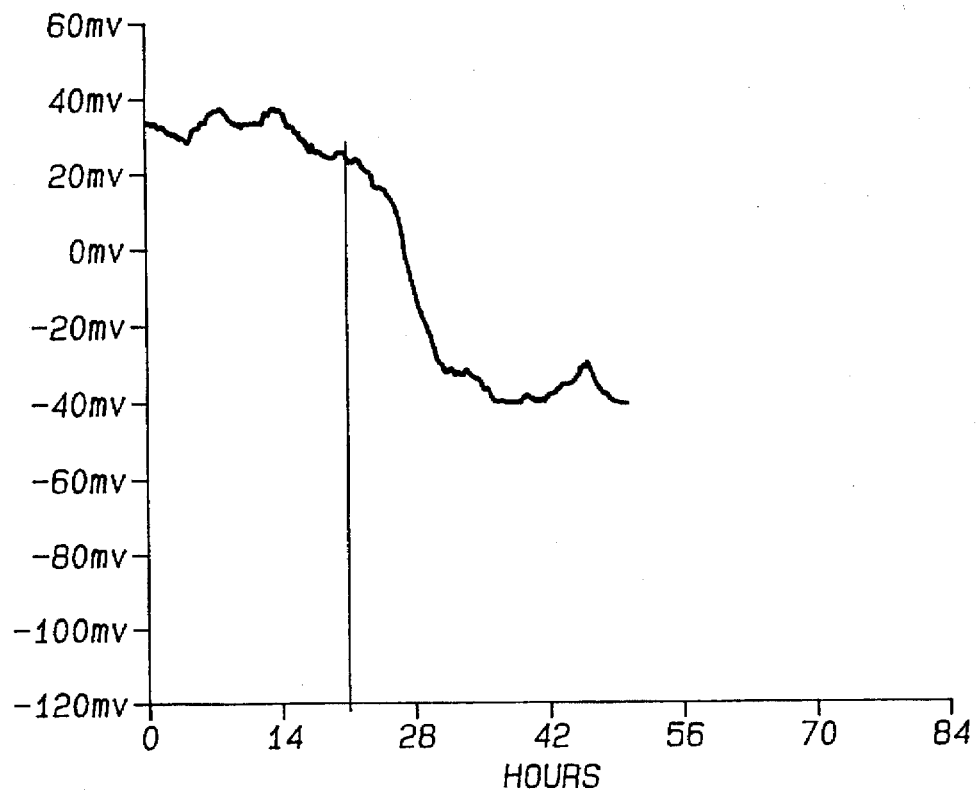
FIG. 2b is a graphic illustration of pressure change in a sample for containing M. tuberculosis in a 20% oxygen environment with the sponge insert.

The present invention generally shown at 10 in FIG. 1 provides a container 10 for use in the detection of aerobic microorganisms such as *Mycobacterium tuberculosis*, *Mycobacterium avium*, and fungi, or other microorganisms capable of growth within an oxygenated environment. The container or vial 10 comprises a bottle having an inner chamber 12 having a bottom surface 14, a head space 16, a cap 18 with a resilient rubber stopper 20, and a non-toxic insert 22 hydrated with microbial growth promoting media 24 disposed within the inner chamber 12 for better dispersion of the microorganisms and to increase microbial exposure to oxygenated media 24 and enhance microbial metabolism. Additionally, the container has a neck portion 26 and a shoulder portion 28.

The container 10 may be constructed of any suitable material such as glass or plastic. Suitable plastics include polystyrenes, polypropylenes, and polycarbonates. Of course, any suitable material must be non-toxic to the microorganisms and be capable of being sterilized by suitable means such as by an autoclave or irradiation. Preferably, the container 10 will be constructed of a transparent material to aid not only in the visual detection of microorganisms but will also allow for a technician or user to visually confirm, prior to introduction of a sample, such as bodily fluid, that the container 10 is free of contamination.

The non-toxic insert 22 is disposed within the inner chamber 12 of the container 10. In the preferred embodiment, the insert is made from highly porous material which greatly increases surface area for microbial exposure to the oxygenated growth media 24. Increasing microbial exposure to oxygenated growth media is a critical feature of the non-toxic insert 22. By increasing exposure to oxygenated media in this manner, shaking of the container is not required. In other words, the insert 22 provides sufficient oxygenation of the growth media 24 to promote and sustain microbial proliferation without the need for other methods of supplemental oxygenation.

In the preferred embodiment, the non-toxic insert 22 is made of sponge. Sponge is an ideal material for the insert means 22 because its high porosity provides for greater oxygenation of the growth media. The large surface area provided by the porosity of the sponge allows for enhanced oxygen exchange between the air and the growth media 24. Other materials for the insert include cotton; fiber glass; glass beads, plastic (resinous material) and sponge beads and Porex™ porous plastics (made of polyethylene, polypropylene, polyvinylidene fluoride, ethylene-vinyl acetate, stryeneacrylonitrite, etc.). It must be noted that whatever material is selected to serve as the insert 22, the material must be non-toxic to microorganisms, that is, the material must be essentially inert and not affect microbial growth.

When hydrated with a sufficient growth media 24, the non-toxic insert 22 occupies between about 25–80% of the volume of the inner chamber 12. By occupying a volume in this range within the inner chamber 12, growth conditions within the container 10 are optimized. In other words, the relationship between growth media 24, surface area, and oxygen are optimal when the hydrated insert 22 occupies a volume of the container 10 within the above-stated range and, therefore, increasing microorganism metabolism. Since a number of aerobic microorganisms grow better suspended in the liquid air interface where $O_2$ is most available, the insert 22 greatly enhances oxygenation of the microbial growth media and, hence, oxygenation of the aerobic microorganisms. Another means of increasing the availability of oxygen is by increasing the oxygen concentration in the headspace.

In essence, the insert 22 establishes an environment with conditions similar to those found in lungs. Establishing an "artificial lung" environment enables growth in vitro of microorganisms, such as M. tuberculosis and M. avium, which were previously difficult to culture in vitro. This effect is also observed with other oxygen requiring microorganisms such as fungi. This micro-environment exposes the microorganisms to highly oxygenated growth media 24 to promote and support microbial growth.

The microbial growth medium 24 comprises all the nutrients required for growth of the target organism. For example, microbiological growth media such as Middlebrook 7H9 is used for growing *Mycobacterium sp*. It is understood by those skilled in the art that the microbiological growth media 24 is chosen based on the particular microorganism being selected for. In other words, the particular microbial growth medium 24 is selected based on biochemical or nutritional requirements of the microorganism one desires to culture.

In addition to the liquid culture medium, the microbial growth medium 24 can include other selective or differential additives such as antibiotics. These additional additives can be used in order to select for the presence of or differentiate particular microorganisms based on specific and unique microorganism characteristics i.e., antibiotic resistance/susceptibility or growth requirements.

The present invention also includes a method for making the container 10 adapted for use in the detection of aerobic microorganisms. The method comprises the steps of inserting an unexpanded non-toxic insert 22 into the container 10. The unexpanded nontoxic insert 22 is preferably a dehydrated and/or compressed sponge material. Additionally, the non-toxic insert 22 can be an unfoamed or unexpanded material such as polyurethane which is inserted into the container 10. Once inside the container 10, the unexpanded non-toxic insert 22 is expanded by means known in the foaming art. Glass or plastic (resin) beads as well as sponge beads can also be added to containers. All the insert materials serve the same purpose of increasing the oxygen media interface thereby allowing more available oxygen to the microorganisms.

When foam is used for the insert, expanding the unexpanded non-toxic insert 22 within the container 10 includes the step of rehydrating the sponge material with microbial growth media 24 such as Middlebrook 7H9 media or other suitable growth media. Thus, upon expansion, the insert 22 is hydrated throughout with media thereby providing a homogenous growth promoting environment throughout the material.

Foamable material can be cast within a bottle followed by the addition of media. It is critical that the material used for the insert 22 be non-toxic to microorganisms as previously described above.

The present invention also includes a method for detecting aerobic microbiological growth in a sealed sampled container 10 having a headspace 16, and non-toxic insert 22 therein saturated with microbiological growth media 24. The method includes the steps of providing a sealed sample container 10 having a headspace 16 and non-toxic insert 22 saturated with microbiological growth media 24. The insert 22 disposed within the sealed sample container 10 is inoculated with a sample, such as a bodily fluid, to be analyzed for the presence or absence of microorganisms. The sealed sample container containing the inoculated insert 22 is monitored for evidence of microbial metabolism.

The sealed sample container 10 containing the insert 22 saturated with microbiological growth media can be provided in a sterile, ready to use form. Additionally, the sealed sample container 10 containing the insert 22 may be obtained in a form in which a sterile, sealed container 10 having a dehydrated insert 22 is provided and the user aseptically adds their own specific or preferred microbiological growth media 24 to the sealed container 10 via the rubber stopper 20.

Inoculation of the insert 22 within the container 10 is generally accomplished by injecting a sample, such as bodily fluid-using a sterile syringe and needle. The needle is pierced through the resilient rubber stopper 20 and the contents of the syringe are injected onto the porous insert 22.

The inoculated container 10 is then monitored for indicia of microbial metabolism such as pressure change in the headspace of the container 10 as a function of rate of changes of headspace pressure, or visual indicia such as changes in turbidity (clarity) of the microbiological growth media 24. This list of possible indicia of microbial metabolism is merely for illustrative purposes and is not intended to be provided as a complete list. Other suitable methods of detecting microbial metabolism known to those skilled in the art may be substituted.

It should be noted that the present invention is not limited to detection of microorganisms in bodily fluid. Various types of samples, such as food stuffs or other industrially tested samples, can be inoculated in the container 10 by means well known in the art.

The following examples illustrate the preparation of, use of and utility of the present invention.

EXAMPLES

Example 1

Materials and Methods

Containers containing sponge material hydrated with an amount of Middlebrook 7H9broth media sufficient to completely wet the sponge (approximately 30 ml) were sterilized by autoclave. The sponge material occupied approximately 80% of the volume of container. Samples containing $2.0\times10^2$ cfu/ml (colony forming units/milliliter) *Mycobacterium tuberculosis* H37RV were inoculated into the containers. The inoculated containers were fitted with a ESP connecter (Difco Laboratories, Inc.) and connected to an ESP machine (headspace pressure sensing device, Difco Laboratories, Inc.) and were statically incubated at 35° C. The initial amount of oxygen in the headspace was 20%. An experimental control was run in tandem with the experimental container and varied on in that it did not contain the sponge material.

Results

Referring to FIGS. 2*a* and 2*b*, after two hundred and ten (210) hours of monitoring the change in headspace pressure, the experimental container including the sponge material insert (see FIG. 2*b*) exhibited a much better and faster signal indicating the presence of a microorganism than did the control container (see FIG. 2*a*). The experimental container displayed a more defined signal to noise ratio than did the control container, that is, the point at which detection was possible was much more distinct for the experimental container than for the control container. This indicates that even in the absence of shaking, exposure of the microorganisms to oxygenated media is enhanced by using the non-toxic insert.

Example 2

Materials and Methods

Containers containing sponge material hydrated with an amount of Middlebrook 7H9broth medium sufficient to completely wet the sponge (approximately 30 ml) were sterilized by autoclave. The sponge material occupied approximately 80% of the volume of container. Samples containing $2.0\times10^2$ cfu/ml (colony forming units/milliliter) *Mycobacterium tuberculosis* H37RV were inoculated into the containers. The inoculated containers were fitted with a ESP connecter (Difco Laboratories, Inc.) and connected to an ESP machine (headspace pressure sensing device, Difco Laboratories, Inc.) and were statically incubated at 35° C. The initial amount of oxygen in the headspace was 40%. An experimental control was run in tandem with the experimental container and varied on in that it did not contain the sponge material.

Results

Referring to FIGS. 3*a* and 3*b*, after two hundred and thirty (230) hours of monitoring the change in headspace pressure, the experimental container including the sponge material insert (see FIG. 3*b*) exhibited a much better and faster signal indicating the presence of a microorganism than did the control container (see FIG. 3*a*). The experimental container displayed a more defined signal to noise ratio than did the control container, that is, the point at which detection was possible was much more distinct for the experimental container. These results also indicate that growth in a higher concentration of oxygen yields faster and more distinctive results i.e., a more definite signal to noise ratio indicating the detection of the presence of microorganisms and, is also indicative of enhanced microbial metabolism.

Example 3

Materials and Methods

Containers containing sponge material hydrated with an amount of ESP medium sufficient to completely wet the sponge (approximately 30 ml) were sterilized by a autoclave. The sponge material occupied approximately 80% of the volume of the container. Samples containing 0.6 cfu/ml (colony forming units/milliliters) *Cryptococcus neoformans* ATCC 14116 were fitted inoculated into the containers. The inoculated containers were with a ESP connector (Difco Laboratories, Inc.) and connected to an ESP machine (headspace pressure sensing device, Difco Laboratories, Inc.) and were statically incubated at 35° C. The initial amount of oxygen in the bottle in the headspace was 20%. An experimental control was run in tandem with the experimental container and varied on in that did not contain the sponge material.

Results

Referring to FIGS. 4a and 4b, after fifty-four (54) hours of monitoring the change in headspace pressure, the experimental container including the sponge material insert (see FIG. 4b) exhibited a much better and faster signal indicating the presence of a microorganism than did the control container (FIG. 4a). The experimental container displayed a more defined signal to noise ratio than did the control container, that is, the point at which detection was possible was much more distinct for the experimental container than for the control container. This indicates that even in the absence of shaking, exposure of the microorganisms to oxygenated media is enhanced by using the non-toxic insert.

Example 4

Materials and Methods

Containers containing sponge material hydrated with an amount of ESP aerobic medium sufficient to completely wet the sponge (approximately 30 ml) were sterilized by a autoclave. The sponge material occupied approximately 80% of the volume of the container. Samples containing 0.6 cfu/ml (colony forming units/milliliter) *Cryptococcus neoformans* ATCC 14116 were inoculated into the containers. The inoculated containers were fitted with a ESP connector (Difco Laboratories, Inc.) and connected to an ESP machine (headspace pressure sensing device, Difco Laboratories, Inc.) and were incubated without agitation at 35° C. The initial amount of oxygen in the headspace was 40%. An experimental control was run in tandem with the experimental container and varied on in that it did not contain the sponge material.

Results

Referring to FIGS. 5a and 5b, after fifty-two (52) hours of monitoring the change in headspace pressure, the experimental container including the sponge material insert (see FIG. 5b) exhibited a much better and faster signal indicating the presence of a microorganism than did the control container (see FIG. 5a). The experimental container displayed a more defined signal to noise ratio than did the control container, that is, the point at which detection was possible was much more distinct for the experimental container. These results also indicate that growth in a higher concentrations of oxygen yields faster and more distinctive results, i.e., a more definite signal to noise ratio indicating the detection of the presence of microorganisms and, is also indicative of enhanced microbial metabolism.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

We claim:

1. A container (10) for detecting aerobic microorganisms in a sample, said container (10) comprising:

a closed chamber (12) defining a headspace above said chamber; and a porous non-toxic insert means (22) having a surface area and being positioned in said chamber (12), and including a microbiological growth media disposed on said insert means thereon, for providing a quantity of oxygen to said media and permitting microorganisms introduced with said sample to reside on said surface thereon by increasing, in a substantially static state, the microorganisms' exposure to oxygen within said chamber and enhancing the microorganisms' metabolism, said insert means being selected from the group consisting of sponge, cotton, fiber glass beads, glass, and resinous material.

2. A container (10) as set forth in claim 1 wherein said insert means is a foamed material.

3. A container (10) as set forth in claim 1 wherein said insert means (22) occupies between 25–80% of said chamber (12).

4. A container as set forth in claim 1 wherein said container (10) includes sealing means for sealing closed said container (10).

5. A method of making a container (10) for detecting aerobic microorganisms in a sample comprising the steps of:

providing a sealable container with a closed chamber, said closed chamber having a headspace;

inserting an unexpanded non-toxic porous insert (22) into said container (10);

adding to said porous insert (22) disposed within said container (10) a microbial growth media (24) while exposing upon sealing said container, said porous insert (22) to said headspace in said container, said porous insert providing a quantity of oxygen to said media for increasing the microorganisms to oxygen exposure and enhancing the microorganisms' metabolism; and sterilizing said media.

6. The method as set forth in claim 5 further comprises the step of increasing oxygen in the headspace of the container.

7. A method of detecting the presence of aerobic microbiological growth in a sealed sample container (10) having a headspace (16) containing a sample which contain unknown microorganisms, said method comprising the steps of:

(a) providing a sealed sample container (10) having a headspace (16) and a non-toxic insert (22) including a microbiological growth media disposed on said insert thereon, for providing a quantity of oxygen to said media, said insert having a surface area for exposing the microorganisms to oxygen within said container and enhancing the metabolism of the microorganisms, said insert being selected from the group consisting of sponge, cotton, fiber glass beads, glass, and resinous material;

(b) inoculating said insert (22) within said sealed container (10) with said sample containing said unknown microorganisms; and (c) monitoring the metabolism within said container (10) as an indicator of the presence of said microorganisms to detect said microorganisms in said sample, while maintaining said container and said insert in a static state during said monitoring step.

8. A container (10) for detecting aerobic microorganisms in a sample, said container (10) comprising:

a closed chamber (12) containing a growth media (24) therein and defining a headspace above said media; and a non-toxic insert means (22) hydrated with said growth media (24) having a surface area positioned within said chamber (12) and at least partially into said headspace for providing a quantity of oxygen to said growth media and permitting microorganisms introduced with said sample to reside on said surface thereon by increasing, in a substantially static state, the microorganisms' exposure to oxygen within said chamber and enhancing the microorganisms' metabolism, said insert means being selected from the group consisting of sponge, cotton, fiber glass beads, glass, and resinous material.

* * * * *